United States Patent [19]

Chung et al.

[11] Patent Number: 5,286,800
[45] Date of Patent: Feb. 15, 1994

[54] OLEFIN GRAFT COPOLYMERS PREPARED USING BORANE-CONTAINING OLEFIN BACKBONE POLYMERS

[75] Inventors: T. C. Chung; G. J. Jiang; D. Rhubright, all of State College, Pa.

[73] Assignee: The Pennsylvania Research Corporation, University Park, Pa.

[21] Appl. No.: 863,632

[22] Filed: Apr. 6, 1992

[51] Int. Cl.$^5$ .................. C08F 255/00; C08F 279/00
[52] U.S. Cl. .................. 525/288; 525/279; 525/296; 525/301; 525/302; 525/309; 525/310; 525/317
[58] Field of Search ............... 525/279, 288, 296, 301, 525/302, 309, 310, 317; 526/239, 336, 348.7, 352

[56] References Cited

U.S. PATENT DOCUMENTS

| | | | |
|---|---|---|---|
| 3,862,102 | 1/1975 | Milkovich et al. | 525/288 |
| 4,638,092 | 1/1987 | Ritter | 526/178 |
| 4,751,276 | 6/1988 | Chung | 526/239 |
| 4,806,581 | 2/1989 | Walker | 525/310 |
| 5,180,788 | 1/1993 | Vroomans | 525/310 |

*Primary Examiner*—Vasu S. Jagannathan
*Attorney, Agent, or Firm*—Thomas J. Monahan

[57] ABSTRACT

Polyolefin graft copolymers are disclosed which comprise a polyolefin homopolymer or copolymer backbone polymer having a plurality of free radically polymerized polymeric segments chemically bonded as side chains. It has been found that the use of a borane-containing polyolefin comprising a copolymer of at least one alpha-olefin having from about 2 to 22 carbon atoms copolymerized with another monomer containing organoborane functional groups can be used as a backbone polymer to prepare the graft copolymers of the present invention. Under oxidation conditions, the borane group becomes the reaction site for the free radical polymerization and copolymerization. Numerous free radical polymerizable monomers, such as methyl methacrylate, styrene, alpha-methylstyrene, acrylonitrile and the like, can be polymerized to yield high molecular weight graft copolymers. By this synthetic route, high graft efficiency is observed with only a very low concentration of homopolymer being produced.

17 Claims, No Drawings

OLEFIN GRAFT COPOLYMERS PREPARED USING BORANE-CONTAINING OLEFIN BACKBONE POLYMERS

BACKGROUND OF THE INVENTION

1. Field of the Invention

This invention relates to graft copolymers. More particularly, the present invention relates to graft copolymers including an olefin backbone polymer and a free radical polymerized polymer grafted thereto made using a borane-containing polyolefin as the backbone polymer.

2. Description of Related Art

Although useful in many commercial applications, polyolefins suffer the major deficiency of poor interaction with other materials. The inert nature of polyolefins significantly limits their end uses, particularly those in which adhesion, dyeability, paintability, printability or compatibility with other functional polymers is paramount. The poor compatibility of polyolefins is further evidenced in their use as coatings where weak adhesion between polyolefins and metal surfaces has not allowed the facile use of this material for the protection of metal. Furthermore, attempts to blend polyolefins with many other non-olefin-based polymers have been unsuccessful because of the incompatibility of the two polymers.

It has been demonstrated that the addition of polar groups to polyolefin polymer structure can improve the adhesion of polyolefin to many substrates, such as metals and glass. In polymer blends, the compatibility of the polymers can be improved by adding a suitable compatibilizer which alters the morphology of these blends. To be successful, it is necessary to reduce the domain sizes for both of the polymers and to increase the interaction between domains.

It is possible to use block or graft copolymers as compatibilizers in such situations as, for example, disclosed in U.S. Pat. No. 4,299,931; Macromolecules 15,370, 1982; Macromolecules 12,131, 1979; J. Polym. Sci, Polym Phys. 18, 2148, 1980; and U.S. Pat. No. 4,174,358. Most block copolymers have been produced by sequential living polymerization processes, particularly anionic polymerization, but such processes are limited to a relatively limited class of monomers. A number of the techniques used to produce these graft or block copolymers are inefficient, resulting in ill-defined products caused by gel formation, backbone degradation, the formation of homopolymers, uncontrolled graft density and molecular weight. These deficiencies are even more pronounced for polyolefins due to their inert nature and difficulties in functionalization reactions involving such polymers. As a consequence, polyolefins have been the most difficult materials to chemically modify, both by functionalization and graft reactions.

This inertness may be overcome to some extent by incorporating polar (functional) groups into polyolefin materials and several techniques for accomplishing this are known. One technique involves oxidizing the polymer backbone by irradiation or contact with a free radical generator (organic peroxide) and then contacting the activated polymer with an unsaturated polar compound such as maleic anhydride. However, such processes can lead to degradation of the polymer backbone during the treatment process. Another technique involves forming copolymers of alpha olefin monomers and copolymerizable monomers containing polar groups.

Among the polyolefins, polypropylene is generally more difficult to functionalize by copolymerization processes. because crystalline polypropylene is made only using Ziegler/Natta catalysts, it is generally difficult to impart functionality to the polymer by copolymerization techniques because polar groups present in the comonomers tend to be reactive with the catalyst system, rendering the catalyst inactive and poisoning it.

U.S. Pat. No. 3,492,277 discloses prereacting a polar monomer such as undecylenic acid, alcohol or amide with an organo aluminum compound thereby rendering such monomers less reactive with Ziegler catalysts. This facilitates their use in forming Ziegler catalyzed alpha olefin copolymers. A similar technique is disclosed in U.S. Pat. No. 4,518,757 wherein copolymers are prepared comprising an alpha olefin and an acid ester comonomer such as methyl-10-undecenoate ester.

More recently, versatile homopolymers and copolymers based on borane-containing monomers have been disclosed. U.S. Pat. Nos. 4,734,472 and 4,751,276 disclose borane-containing monomer material prepared by reacting a diolefin and a dialkyl borane solution. These monomers may be polymerized using Ziegeler-Natta catalysts to form polyborane homopolymers or random copolymers of 1-octene and the borane-containing monomer.

Block or blocky copolymers of propylene and such borane-containing monomers are the subject of copending application Ser. No. 07/637,410, filed on Jan. 4, 1991.

The chemistry involved in the above-mentioned patents and application is the direct polymerization using organoborane-substituted monomers and alphaolefins in Ziegler-Natta processes. The homo- and copolymers containing borane groups are very useful intermediates to prepare a series of functionalized polyolefins.

The essential advantages of this chemistry are (a) the stability of the borane moiety to transition metal catalysts, (b) the solubility of borane compounds in hydrocarbon solvents (hexane and toluene) used in transition metal polymerizations, and (c) the versatility of borane groups which can be transformed to a wide variety of functionalities, as disclosed by H. C. Brown, Organic Synthesis via Boranes; Wiley-Interscience; New York, 1975. Many new functionalized polyolefins with various molecular architectures may be obtained based on this chemistry.

It is also known that trialkyborane in an oxidated state becomes an initiator for the polymerization of a number of vinyl monomers, as disclosed by J. Furukawa et al., J. Polymer Sci, 26, 234, 1957; J. Polymer Sci. 28,227, 1958; Makromol. Chem., 40, 13, 1961; F. J. Welch, J. Polymer Sci. 61,243, 1962; and in U.S. Pat. No. 3,476,727. The polymerization mechanism involves free radical addition reactions. The initiating radicals may be formed from homolysis of peroxyborane or by the redox reaction of the peroxyborane with unoxidized trialkylborane. A major advantage in borane initiators is the ability to initiate polymerization at low temperature. Peroxides and azo initiators when used alone usually require considerable heat input to decompose and thereby to generate free radicals. Elevation of the reaction temperature often causes significant reduction in polymer molecular weight accompanied by the loss of important properties of the polymer.

U.S. Pat. No. 3,141,862, discloses conducting a trialkylborane-initiated free radical polymerization in the presence of a polyolefine polymer. Apparently, the graft reaction by this route was very difficult. The inert nature and insolubility of polyolefin (due to crystallinity) also seems to have hindered the process and resulted in very poor graft efficiency. The reactions shown in the examples of this patent also seem to require a very high concentration of organoborane initiator and monomer and require elevated temperature. The majority of the products are homopolymers or insoluble gel. No information about the molecular structure of the copolymers is given.

Despite the advantages of borane initiators, organoborane-initiated polymerizations tend to be unduly sensitive to the concentration of oxygen in the polymerization system. Too little or too much oxygen results in little or no polymerization. High oxygen causes organoborane to be rapidly transferred to borinates, boronates and borates which are poor initiators at low temperatures. Moreover, polymerization is often inhibited by oxygen. To facilitate the formation of free radicals, U.S. Pat. Nos. 4,167,616 and 4,638,092 disclose that borane containing oligomers and polymers may be used as initiators in such free radical polymerizations. These organoboranes are prepared by the hydroboration of diene monomer or polymers or copolymers. The similar polymeric organoborane adduct, prepared by the hydroboration of 1,4-polybutadiene and 9-borabicyclo(3,3,1)-nonane has also been reported in Macromol. Chem. 178, 2837, 1977. However, no information was provided about the applications of organoborane-containing polyolefin polymers in the preparation of polyolefin graft copolymers.

SUMMARY OF THE INVENTION

In this invention, new polyolefin graft copolymers have been discovered which comprise a polyolefin homopolymer or copolymer backbone polymer having a plurality of free radically polymerized polymeric segments chemically bonded as side chains. Most particularly in accordance with this invention, it has been found that the use of a borane-containing polyolefin comprising a copolymer of at least one alphaolefin having from about 2 to 22 carbon atoms copolymerized with another monomer containing organoborane functional groups can be used as a backbone polymer to prepare the graft copolymers of the present invention. Under oxidation conditions, the borane group becomes the reaction site for the free radical polymerization and copolymerization. Numerous free radical polymerizable monomers, such as methyl methacrylate, styrene, alphamethylstyrene, acrylonitrile and the like can be polymerized to yield high molecular weight graft copolymers. By this synthetic route, high graft efficiency is observed with only a very low concentration of homopolymer being produced.

DETAILED DESCRIPTION OF THE INVENTION

Graft copolymers prepared in accordance with this invention may be generally characterized by formulas I or II as follows:

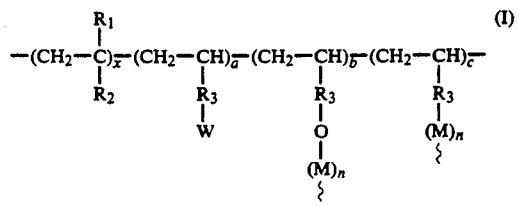

and

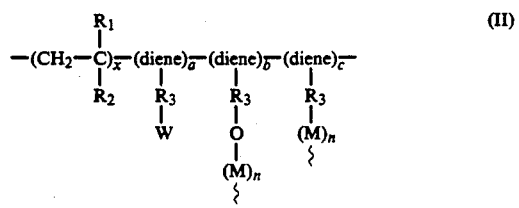

wherein $R_1$ and $R_2$ are the same or different and are selected from the group consisting of $H, C_1$ to $C_{20}$ alkyl, phenyl and alkyl substituted phenyl; $R_3$ is a direct link or a divalent hydrocarbon having from 1 to 20 carbon atoms of linear or branched structure; W is a polar substituent group; M is a free radically polymerizable monomer; n is the degree of polymerization of M ranging from 1 to about 70,000; (diene) is a recurring segment of a polymerized diolefin monomer; x range from about 50 to about 70,000; (a) ranges from 0 to about 20,000; and the sum of (b) and (c) ranges up to about 20,000 with the proviso that (b) or (c) is at least 1 when the other of (b) or (c) is 0.

It is to be understood from the above formula that not all of the (b) and/or (c) segments of the polymer chain contain graft chains attached thereto, in which case the graft copolymers will contain some (a) segments as well. Polar group W is preferably selected from the group consisting of OH, $NH_2$, CHO, halogen or $BR_4R_5$ wherein $R_4$ and $R_5$ are the same or different alkyl or cycloclkyl groups containing from 1 to about 10 carbon atoms. These groups may serve as a crosslinking site involving crosslinking reactions between the graft copolymers with themselves or with other functionalized polymers.

The reactive backbone of these graft copolymers may be prepared by either of two processes. Backbone polymers corresponding to formula I above may be prepared by direct copolymerization of a borane-containing monomer with one or a mixture of alpha-monoolefins using a Ziegler/Natta catalyst system. Backbone polymers responding to formula II above are prepared by reacting a preformed polymer containing residual unsaturation along the polymer chain with a hydroboration agent.

The borane-containing monomers which are useful in preparing the backbone copolymers of formula 1 above may be generally categorized by the formula:

wherein m is an integer ranging from 3 to 12, and $R_4$ and $R_5$ are the same or different alkyl or cycloalkyl groups containing 1 to 10 carbon atoms. This monomer is prepared as the addition product of 9-borobicyclononane (hereinafter referred to as 9-BBN) and a diene having the structure $CH_2=CH-(CH_2)_z-CH=CH_2$ wherein z ranges from 1 to 10. Preferred dienes are those wherein z ranges from about 1–4 and included 1,7-octadiene, 1,5-hexadiene and 1,4-pentadiene, with 1,5-hexadiene being most preferred. The reaction is preferably conducted at a temperature of from about −10° to 50° C. by slow addition of a solution of 9-BBN in suitable solvent such as tetrahydrofuran (THF) to a 2-6 molar excess of the diene material under an inert blanket such as argon or nitrogen, and allowing the reaction to proceed under mild agitation for a period of at least about 1 hour, preferably at least about 2–5 hours.

These monomers and the methods of synthesis are also disclosed in U.S. Pat. No. 4,751,276, the disclosure of which is incorporated herein by reference.

Alpha monoolefins which may be copolymerized with the borane-containing monomers include one or a mixture of $C_2$ to $C_{20}$ olefins, including ethylene, propylene, 1-butene, isobutene, 1-hexane, 1-octene and the like.

The direct copolymerization is usually carried out by a Ziegler-Natta process by mixing the olefin monomer and borane monomer with Ziegler-Natta catalyst. The preferred borane monomer includes but is not limited to B-(7-octen-1-yl)-9-BBN; B-(5-hexen-1-yl)-9-BBN; and B-(4-penten-1-yl)-9-BBN. The Ziegler-Natta catalyst employed may include halides or alkoxyhalides of a transition metal, such as titanium, zirconium, vanadium, chromium and molybdenum, and a cocatalyst such as triethylaluminum, diethylaluminum chloride and ethylaluminum dichloride. The polymerization is usually carried out between 0° to 50° C. in neat or in hydrocarbon solvents such as hexane, heptane and toluene. The level of incorporation of the borane monomer into the resulting polyolefin may range from 0.1 to 50% by mole, preferably from 0.1 to 5% by mole.

Polymers of formula II above are prepared by the hydroboration of preformed olefin copolymers containing residual unsaturation along the polymer chain. Examples of preferred backbone polymers include copolymers of one or more $C_2$ to $C_8$ monoolefins with a conjugated or non-conjugated diene such as butadiene, isoprene, piperylene, norbornadiene, dicyclopentadiene, 1,4-hexadiene, 5-methylene-2-norbornene, 5-ethylidene-2-norbornene and like materials. These polymers are generally elastomeric in nature and include such materials as isobutylene/isoprene copolymers (butyl rubber) and terpolymers of ethylene/propylene and a non-congugated diene such as 1,4-hexadiene or 5-ethylidene-2-norbornene. Preferred such polymers contain from about 0.1 to about 15% by weight of the diene component, more preferably from about 1 to 5% by weight.

Hydroboration reagents which may be used to prepare the hydroborated polymer include boron hydride species such as diborane, 9-BBN, dimethyl borane, dichloroborane, catecholborane and other species which are reactive to double bonds and which are disclosed, for example, in U.S. Pat. No. 4,167,616 or 4,638,092 referred to above.

Hydroboronation may be readily carried out by dissolving the elastomeric polymer in suitable solvent, adding stoichiometric or larger quantities of the hydroboronation reagent to the solution and heating the solution to effect reaction of the boronating reagent with at least some of the double bonds present in the polymer backbone.

The subsequent graft polymerization reaction is a free radical polymerization initiated by simultaneously exposing the borane-containing polyolefin to an oxidative reagent, including but not limited to oxygen, air, $H_2O_2$, cumene hydroperoxide, t-butylhydroperoxide and metal oxides such as $CuO$, $MnO_2$ and $V_2O_5$, and at least one monomer which is polymerizable by a free radical polymerization process. If oxidation agents are not included in the graft reaction system, the polymerization occurs very slowly. The preferred amount of oxidative reagent is stoichiometric to the borane groups present in the polyolefins. The free radical polymerization may be carried out at a temperature between 0° to 80° C., preferably from about 0° to 30° C., in neat or in common solvents such as THF, diethyl ether, cyclohexane, heptane, benzene and toluene. Free radically polymerizable monomers which may be used as the grafting monomer include, but are not limited to vinyl monomers such as methacrylates and alkyl acrylates, including methyl and tert-butyl methacrylates and acrylates, acrylic and methacrylic acids, vinyl aromatic compounds such as styrene, alpha-methylstyrene, para-methylstyrene, vinyl toluene and its isomers, vinyl amides such as acrylamide and methacrylamide, vinyl pyridine, acrylonitrile, methacrylonitrile, vinyl acetate, vinyl chloride, and vinylidene chloride. Polymerizable olefin monomers such as ethylene may also be used.

The graft polymerization process may be depicted as follows:

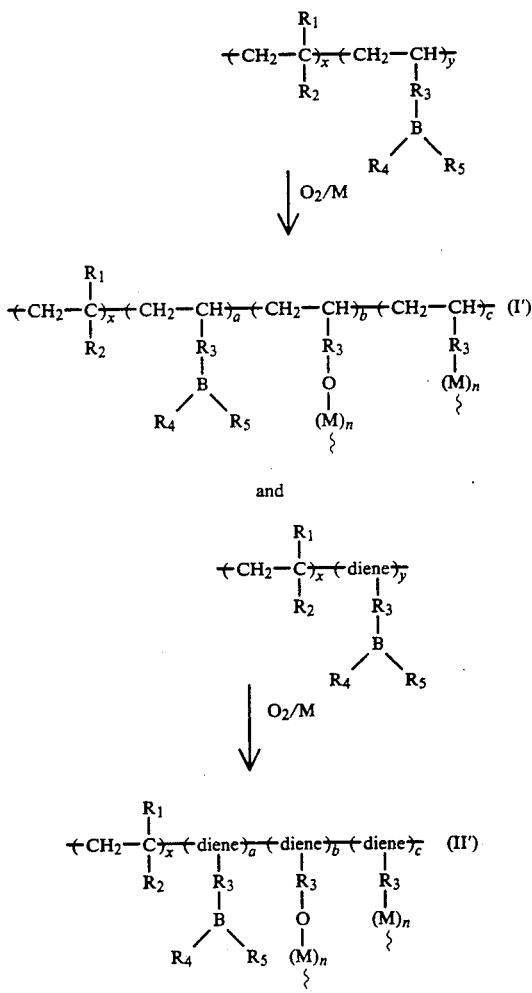

wherein y represents the number of monomer repeating units and is equal to (a)+(b)+(c) and $R_1$, $R_2$, $R_3$, $R_4$, $R_5$, x, a, b, c, M and n are as set forth above.

Graft copolymers in accordance with this invention may be prepared having a number average molecular weight (Mn) in the range of from about 50,000 to about 3,000,000, preferably from abut 75,000 to 1,500,000 and more preferably from about 100,000 to about 1,000,000. The graft density of the side chains (number of graft chains per molecule of backbone polymer) will vary from between 0.1 to about 75% per backbone monomer repeating unit as a function of the mole % of organoborane repeating units present in or introduced into the backbone polymer. In addition, the Mn of the grafted side chains may range from about 500 up to about 500,000. As a general rule, it is preferred that where the graft density of side chains is below 1%, then the molecular weight of the side chains be above about 10,000; where the graft density of the side chains is above about 10%, then the molecular weight of the side chains is below about 2,000.

The preferred content of free radically polymerized graft polymer present in the copolymers generally may range from about 5 to about 95% by weight based on the total copolymer weight, with about 10 to about 80% by weight being the most preferred range.

As previously indicated, graft polymers having the structure I' and II' immediately above wherein (a) is at least 1 can be readily converted into graft polymers having the structure I and II shown earlier wherein (a) is at least 1 by reaction with an appropriate reagent under mild conditions to introduce a polar substituent W into the polymer chain. Preferred polar substituents include OH, halogen such as iodine, CHO and $NH_2$. For example, the borane-containing copolymer, suspended in solvent, can be reacted with a mixture of an organic base and a peroxide to form alcohol substituent groups displacing the borane radical.

Similarly, polymers containing amino functionality may be prepared by reaction of the borane-containing polymer with $NH_2OSO_3R$; polymers containing aldehyde functionality may be prepared by reaction of the borane-containing polymer with a mixture of CO and $K(i-C_3H_7O)_3BH$; and polymers containing iodine functionality may be prepared by reaction of the borane-containing polymer with a basic solution of NaI/chloramine-T hydrate. Other such reactions are disclosed by Brown, H. C., Organic Synthesis via Boranes; Wiley-Interscience: New York, 1975, the relevant portions of which are incorporated herein by reference.

Unmodified borane-containing polymers of the formula I or II above wherein W is $B-R_4R_5$ can utilize the borane groups as crosslinking sites by exposing the borane-containing graft copolymer to a large excess of oxidative reagents such as air or peroxides. This process can be completed in-situ during the grafting reaction. In such a case the polymers become crosslinked by intermolecular linkages at the W sites.

Graft polymers prepared in accordance with this invention have a number of uses. They are soluble in many organic solvents and can be shaped into films or fibers. They may be used as compatibilizers for polymer systems based on blends of polyolefin polymers and other polymers with which the polyolefins are not normally compatible such as polyamides, vinyl aromatic polymers, polyesters and similar polar polymers. They also find utility as adhesives to promote interfacial bonding between polyolefin polymer sheets, films or fibers and substrates such as other polymeric surfaces, glass, aluminum and other metals to which polyolefins do not readily adhere.

The graft copolymers may also be used to enhance the bonding between polymer matrix systems and reinforcing fillers and fibers such as carbon black and carbon or glass fibers. Inclusion of minor amounts of these graft copolymers in a polymer matrix with which the copolymers are compatible promotes good adhesion of the matrix system to fiber or filler by virtue of the polar nature of the polymer segments present in the graft copolymer side chains.

The following examples are illustrative of the invention.

EXAMPLE 1

Synthesis of hexenyl-9-BBN

This reaction is based on the monohydroboration of 1,5-hexadiene. In an argon filled dry box, 15.092 g (0.124 moles) of 9-BBN dimer crystals were dissolved in 100 ml of dry-degassed THF and added dropwise over 2 hours to 44.515 g (0.542 moles) of 1,5 hexadiene. The solution was stirred at room temperature for 12 hours before any unreacted diene and the THF were removed under vacuum. Another 10.754 g (0.088 moles) of 9-BBN were added to the isolated hexadiene and THF solution as before. Again after 12 hours the unreacted diene and the remaining clear oil fractions were combined and distilled under vacuum. The second fraction collected at 68° C. at 11 umHg was a clear sightly viscous liquid which proved to be pure hexenyl-9-BBN by $^1H$ and $^{11}B$ NMR. 36.01 g were collected for a 73.1% yield.

EXAMPLE 2

Synthesis of polyoctene co-hexenyl-9-BBN

In a typical example, a half liter flask was charged with Ziegler-Natta catalyst, $TiCl_3AA$ (0.08 g, 0.4 mole) and $AlEt_2Cl$ (2.5 mole, 0.3 g) and toluene (50 ml) under argon atmosphere. After aging for 30 min with sufficient mixing, the monomer mixture of 1-octene (11.2 g) and 1-hexenyl-9-BBN (0.101 g) in 150 ml of toluene, monomer mole ratio of 1000 to 5, was added to the catalytic solution. The copolymerization reaction was observed within 5 minutes with visible increase in viscosity. The solution was stirred at room temperature for one hour before the reaction was terminated with isopropanol (300 ml). The precipitate was collected by filtration, washed with isopropanol three times and vacuum dried overnight to yield 5.1 g of copolymer.

Trialkylborane in the copolymer was characterized by $^{11}B$ NMR with chemical shift sigma=87 ppm from $BF_3OEt_2$. A total of six different copolymers, polyoctene-co-hexenyl-9-BBN, were prepared by these procedures and are identified as A1 through A6 in Table 1.

TABLE 1

| | Summary of the Copolymerization of 1-octene and 1-hexenyl-9-BBN | | | | | |
|---|---|---|---|---|---|---|
| | | | | Product/Copolymer | | |
| Sample # | Monomer Feed* (mole ratio) | Reaction** time (min.) | Borane*** (mole %) | Yield (%) | Mn ($\times 10^{-3}$) | Mw/Mn |
| A1 | 1,000/5 | 30 | 0.2 | 45 | 320 | 6.3 |
| A2 | 100/1 | 20 | 0.4 | 34 | 310 | 5.8 |

TABLE 1-continued

Summary of the Copolymerization of 1-octene and 1-hexenyl-9-BBN

| Sample # | Monomer Feed* (mole ratio) | Reaction** time (min.) | Borane*** (mole %) | Product/Copolymer Yield (%) | Mn ($\times 10^{-3}$) | Mw/Mn |
|---|---|---|---|---|---|---|
| A3 | 4/1 | 20 | 5 | 20 | 280 | 6.5 |
| A4 | 3/1 | 120 | 15 | 60 | 242 | 6.1 |
| A5 | 1/1 | 120 | 40 | 55 | 126 | 7.8 |
| A6 | 1/3 | 120 | 65 | 52 | 66 | 6.0 |

*octene/1-hexenyl-9-BBN
**room temperature reaction.
*** mole % of borane monomer The analysis of the above organoborane-containing copolymers, such as borane concentration and molecular weight of copolymer, was done in their corresponding hydroxylated copolymer form. The oxidation reaction was carried out by dissolving the organoborane-containing copolymer in THF solution. After adding 6N sodium hydroxide, hydrogen peroxide (30%) was dropped in over a period of 15 minutes. After stirring the mixture at 55° C. for half hour, water was added and the precipitate was collected by filtration and washed with water. Further purification was carried out by redissolving the copolymer in THF, reprecipitating by acetone and drying in vacuum overnight to obtain the desired product. In $^1$H NMR spectrum, the integrated intensity between the chemical shifts sigma = 3.6 ppm ($CH_2$—O) and sigma = 0.8-2 ppm (rest of protons in the copolymer) offer the functional group concentration in the copolymer.

EXAMPLE 3

Preparation of Polyoctene-g PMMA

The polyoctene-co-hexenyl-9-BBN copolymer of Example 2, sample A1, was used to prepare polyoctene-g-polymethylmethacrylate (Polyoctene-g-PMMA) graft copolymer by a free radical graft-from reaction. In a nitrogen atmosphere, 2 g of copolymer A1, dissolved in 50 ml of THF, was mixed with 50 ml of pure methymethacrylate (MMA) monomer in a 200 ml flask. A septum was installed to the flask to isolate the mixture from air. The graft-from reaction occurred after injecting 5 ml of air into the flask by syringe. A notable increase in solution viscosity was observed within a few minutes. The reaction mixture was stirred at ambient temperature and became very sticky after one hour. About 1 ml of reaction mixture was sampled and injected into 10 ml of isopropanol. The resulting precipitate was collected by filtration. Additional washing with isopropanol was continued three times. To remove the possible polymethylmethycrylate (PMMA) homopolymer in the precipitate, a solvent extraction procedure was carried out using acetone solvent. Almost no PMMA homopolymer was extracted out after stirring the mixture at room temperature for 24 hours. The product was then dried in vacuum overnight yielding a graft copolymer which was very soluble in THF solvent. Based on the IR and $^1$H NMR studies, the graft copolymer consisted of 50 mole % of PMMA side chains. The graft-from reaction was continued by redissolving this polymer in THF and continuing the polymerization as described above for two hours before exposing the mixture to ambient atmosphere. The product was precipitated by adding 100 ml of isopropanol. The same purification processes to remove impurities and PMMA homopolymer were repeated as above to obtain 42 g of Polyoctene-g-PMMA with 75 mole % of PMMA side chains in the copolymer.

The detail molecular structure of Polyoctene-g-PMMA was measured by IR, $^1$H NMR and GPC techniques. IR spectrum showed a strong $v_{c=o} = 1720$ cm$^{-1}$ peak, corresponding to carbony groups in PMMA. The quantitative analysis was obtained by $^1$H NMR spectrum, the integrated intensity comparison between the chemical shifts sigma = 3.6 ppm ($CH_3$—O) and sigma = 0.8-2 ppm (rest of protons in the copolymer) offers the PMMA concentration in the polyoctene-g-PMMA copolymer. The average chain length of PMMA in the side chain of the graft copolymer can be estimated by the weight increase during the graft from reaction divided by the moles of organoborane groups in the starting polyoctene-co-hexenyl-9-BBN copolymer. Assuming all organoborane groups are involved in the polymerization, the average molecular weight of PMMA is above 60 000 g/mole.

The thermal properties of the copolymer were evaluated by DSC measurement. The DSC curve of polyoctene-g-PMMA copolymer (with 50 mole % of PMMA) shows two glass transition temperatures (Tg) $-58°$ C. and 113° C., corresponding to the glass transition temperatures of the two homopolymers respectively. This data indicates a phase separation in the copolymer and that the polymer chain length in both polymer segments is quite long resulting in the formation of polyoctene and PMMA domains.

EXAMPLE 4

Preparation of Polyoctene-g-PMMA

Following the general procedure set forth in Example 3, sample A2 in Example 2, which has a 0.4 mole % content of hexenyl-9-BBN in the copolymer, was used to prepare a graft copolymer of Polyoctene-g-PMMA. Two processes of introducing air to the reaction mixture were carried out to study the graft-from reaction.

(a) Slow diffusion of air into the reaction system

In a 200 ml flask, sample A2 (1 g) was dissolved in 70 ml of THF, then 3 ml of pure MMA was added. The graft polmerization took place under very slow diffusion of air through the septum. Air was leaked into the reactor very slowly and the formation of the free radical was also very slow. After one day at ambient temperature, 1 ml of reaction mixture was sampled and purified by the same procedures described in Example 3. The resulting graft copolymer was found to consist only of 2 mole % of PMMA. Under the same reaction condition for two days, about 8 mole % of PMMA was observed in copolymer. After five days reaction time, 30 mole % of PMMA was grafted to the copolymer. In all samples, an almost undetectable amount of PMMA homopolymer could be extracted out by acetone solvent. The graft copolymers were also soluble in THF solvent. The graft-from reaction was obviously continuing during the entire process with slowly increasing levels of oxygen introduced into the reactor.

(b) Expose the reaction system to air

Preparing the same reaction mixtures as described above, sample A2, MMA and THF was mixed in a 200ml flask. The system was however immediately exposed to air. After 10 minutes at room temperature, the sampled polymer was analyzed to have 10 mole % of PMMA, which increased to 16 mole % of PMMA after another 10 minutes.

EXAMPLE 5

Preparation of Polyoctene-g-PMMA

Following the procedure set forth in Example 3, sample A3 in Example 2, which has 5 mole % of hexenyl-9-BBN in the copolymer, was used to prepare the graft copolymer of polyoctene-g-PMMA. The borane containing polymer (0.73 g) was dissolved in 100 ml of THF. 3 ml of pure MMA (MMA/Borane=50/1) was added to the copolymer solution. The graft polymerization took place under slow diffusion of $O_2$ from air through the airtight septum. After 2 hr, the reaction was terminated by pumping out the MMA and solvent in the vacuum line. 1.57 g of PMMA grafted copolymer was obtained. The unreacted borane in the copolymer was oxidized to hydroxyl groups by $NaOH/H_2O_2$ to obtain a grafted copolymer containing 10 mole % of PMMA.

EXAMPLE 6

Preparation of Polyoctene-g-PMMA

Following the procedure set forth in Example 3, sample A3 in Example 2, which has 5 mole % of hexenyl-9-BBN in the copolymer, was used to prepare the graft copolymer of polyoctene-g-PMMA. The borane containing copolymer A3 was dissolved in 50 ml of THF before adding 6.62 g of purified MMA (77 mmole) (MMA/Borane=10/1). The graft polymerization took place under slow diffusion of $O_2$ from air through the septum. The reaction was held at room temperature overnight. After one day, 25 ml of air was injected into the solution mixture and reacted for one more day. The unreacted borane in the copolymer was oxidized to hydroxyl groups by $NaOH/H_2O_2$ reagents. Some of the product formed a microemulsion in the aqueous phase. The precipitated portion (about ⅓) contained about 15% by weight of PMMA. The rest (about 2/3) forming a microemulsion in water was isolated by adding NaCl into the solution. The graft copolymer obtained in this portion had a PMMA concentration of about 60% by weight.

EXAMPLE 7

Copolymerization of Polypropylene and Hexenyl-9-BBN

Propylene gas (Matheson research grade) was dried over NaOH and $P_2O_5$ columns before condensing into a graduated Schlenk flask containing 0.50 ml of $AlEt_2Cl$ at $-78°$ C. 16. 9 ml of propylene (10.96 g, 0.261 moles) was transferred to a 1000 ml Schlenk flask containing 500 ml of toluene. After warming to room temperature, the flask was brought into a dry-box and contacted with 5.312 g ($2.602 \times 10^{-2}$ moles) of hexenyl-9BBN. 30 ml of aged (½ hour) catalyst slurry containing 0.619 g ($4.1 \times 10^{-3}$ mol) of $TiCl_3$-AA and 2.988 g ($2.48 \times 10^{-2}$ mol) $AlEt_2Cl$ was added to catalyze the copolymerization. The polymerization was terminated after 30 min by the addition of isopropyl alcohol. The polymer was isolated by the addition of cold isopropanol followed by filtration. The white powder was then dried under vacuum to yield 5.778 g of poly(propylene-co- hexenyl-9-BBN) which had about 1 mole % of hexenyl-9-BBN in the copolymer.

EXAMPLE 8

Synthesis of Polypropylene-g-PMMA

In an argon field dry-box, 0.692 g of poly(propylene-co-hexenyl-9-BBN) from Example 7 was placed in a suspension with 4.040 g of dry, degassed methylmethacrylate. The suspension was stirred for ½ hour to wet the polymer particles with MMA. The reaction flask containing the borane copolymer and MMA equipped with only a rubber septa was taken out of the dry-box. After 48 hours of stirring, the suspension had completely gelled into a slightly translucent rubbery material. The solid was washed with acetone in a Soxhlet extractor for 12 hours. Both acetone soluble and insoluble fractions were washed with MeOH before drying under vacuum. The acetone fraction yielded 0.275 g of PMMA as identified by $^1$H-NMR and FTIR. The acetone insoluble fraction of 1.906 g was a white powdery solid which was 66.7% PMMA and 33.3% PP by $^1$H-NMR (run in $d_{10}$-O-xylene at 90° C.).

EXAMPLE 9

Synthesis of Polypropylene-g-PMMA

In an argon filled dry-box, 0.692 g of poly(propylene-co-hexenyl-9-BBN) from Example 7 was placed in a suspension with 4.079 g of MMA and 7.42 g of THF. After stirring for ½ hour in the dry-box, the septa equipped flask was taken out of the box. Immediately 1 ml of $O_2$ was injected into the reaction flask. After 1 hour of stirring, another 1 ml of $O_2$ was added. After 24 hours of stirring, the polymer was isolated by precipitation into MeOH. The polymer was then washed with acetone in a Soxhlet extractor for 12 hours. The acetone soluble fraction yielded 0.423 g of PMMA (as shown by $^1$H-NMR and FTIR). The acetone insoluble fraction yielded 1.496 g of white solid after drying under vacuum which was 52% PMMA and 48% PP by $^1$H-NMR (run in $d_{10}$-O-xylene at 120° c.).

EXAMPLE 10

Synthesis of Polypropylene-g-PMMA

In the dry-box, 0.691 g of poly(propylene-co-hexenyl 9BBN) from Example 7 was placed in suspension in 4.073 g MMA (dry, degassed). The suspension of fine white particles was stirred in the dry-box. After 48 hours, suspension had formed a translucent, highly viscous gel. The polymer gel was washed with acetone in a Soxhlet extractor for 12 hours. Both the acetone soluble and insoluble fractions were washed with MeOH before drying under vacuum. The acetone soluble fraction yielded 0.336 g of PMMA (as identified by FTIR and $^1$H-NMR in $CDCCl_3$). The acetone insoluble fraction yielded 0.830 g of white powder that was 5% PMMA and 95% PP by $^1$H-NMR (run in $d_{10}$-O-xylene at 120° C.).

EXAMPLE 11

Synthesis of Polypropylene-g-Poly(t-butyl methacrylate)

In the argon filled dry-box, 0.4 g of poly(propylene-co-hexenyl-9-BBN) from Example 7 was placed in a suspension with 1.78 g of t-butyl methacrylate (dried over $CaH_2$ and vacuum distilled). After stirring for ½ hour in the dry-box, the septa equipped flask was taken out of the box and stirred at room temperature. Air was very slowly diffused into the flask. Within 8 hours, the suspension viscosity had increased noticeably. By 24 hours, the reaction was stopped and the suspension had become a translucent solid. The solid was broken up and stirred in MeOH for 1 hour and then filtered. The polymer was extracted with acetone in a Soxhlet extractor for 18 hours. The acetone soluble fraction yielded 0.199 g. The acetone insoluble fraction yielded 1.02 g of white solid after drying under vacuum.

EXAMPLE 12

Hydroboration of Poly(isobutylene-co-isoprene)

Under atmosphere, 06. g of commercial butyl rubber, poly(isobutylene-co-isoprene) containing 1.6 mole % of isoprene, was dissolved in 30 ml of THF solvent. The hydroboration reaction was completed by adding 0.013 g of 9-BBN crystal to the solution, then refluxing at 68° C. for 10 hours. The resulting hydroborated butyl rubber in THF solution was used directly for graft reactions to prepare butyl rubber graft copolymers as described below.

EXAMPLE 13

Synthesis of Poly(isobutylene-co-isoprene)-g-Polystyrene

In an argon filled dry-box 0.6 g of poly(isobutylene-co-isoprene) containing 1 mole % of borane groups in THF solution obtained from Example 12, was mixed with 10 g of styrene. After stirring for ½ hour in the dry-box, the septa equipped flask was taken out of the box. Immediately 7 ml of $O_2$ was injected into the reaction flask. After 4 hours of stirring, another 5 ml of $O_2$ was added. The solution was stirred at room temperature for 70 hours. The polymer was isolated by precipitation into MeOH, which was then washed with ethyl acetate in a Soxhlet extractor for 12 hours. The resulting graft copolymer after drying under vacuum overnight was 0.84 g, which had the composition of 30/70 mole ratio between polystyrene and poly(isobutylene-co-isoprene).

EXAMPLE 14

Synthesis of Poly(isobutylene-co-isoprene-g-PMMA

In an argon filled dry-box, 0.6 g of poly(isobutylene-co-isoprene) containing 1 mole % of borane groups in THF solution obtained from Example 12, was mixed with 10 g of methyl methacrylate. After stirring for ½ hour in the dry-box, the septa equipped flask was taken out of the box. Immediately 7 ml of $O_2$ was injected into the reaction flask. After 4 hours of stirring, another 5 ml of $O_2$ was added. The solution was stirred at room temperature for 45 hours. The polymer was isolated by precipitation into MeOH, which was then washed with acetone in a Soxhlet extractor for 12 hours. The acetone soluble fraction yielded 0.54 g of graft copolymer with high concentration of PMMA. The acetone insoluble fraction yielded 1.07 g of white solid after drying under vacuum. The composition had a 46/54 mole ratio between PMMA and poly(isobutylene-co-isoprene) by $^1$H-NMR studies.

What is claimed is:

1. A graft copolymer having the formula selected from:

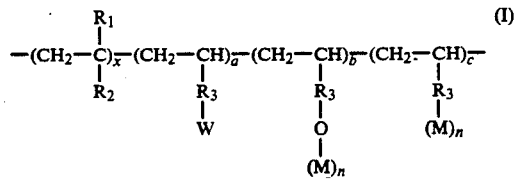

and

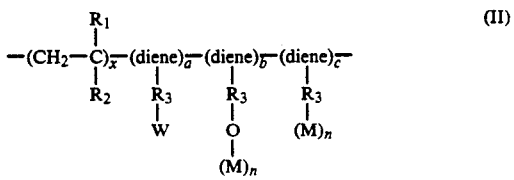

wherein $R_1$ and $R_2$ are the same or different and are selected from the group consisting of H, $C_1$ to $C_{20}$ alkyl, phenyl and alkyl substituted phenyl; $R_3$ is a direct link or a divalent hydrocarbon having from 1 to 20 carbon atoms of linear or branched structure and comprises the residue from a group having the structure $—R_3BR_4R_5$, where $R_4$ and $R_5$ are the same or different alkyl or cycloalkyl group containing from 1 to about 10 carbon atoms and $R_3$ is as defined above; W is a polar substituent group; M is the residue of a free radically polymerizable monomer; n is the degree of polymerization of M ranging from 1 to about 70,000; (diene) is a recurring segment of a polymerized diolefin monomer; x ranges from about 50 to about 70,000; (a) ranges from 0 to about 20,000; and the sum of (b) and (c) ranges up to about 20,000 with the proviso that (b) or (c) is at least 1 when the other of (b) or (c) is 0;

wherein said graft copolymer having the formula I is prepared by:

(i) contacting in the presence of a Ziegler-Natta catalyst a mixture of at least one $C_2$ to $C_{22}$ alpha-monoolefin and a borane-containing monomer having the structure $CH_2=CH(CH_2)_m—BR_4R_5$ wherein m is an integer of from 3 to 12 and $R_4$ and $R_5$ are as described above, to form a copolymer product having borane-containing units in the copolymer chain; and (ii) contacting the copolymer formed in step (i) with at least one free radically polymerizable monomer in the presence of an oxidative reagent to convert at least one of said borane-containing units to a free radical which, in turn, initiates free radical polymerization of said free radically polymerizable monomer, thereby forming said graft copolymer having the formula I; and, wherein said graft copolymer having the formula II is prepared by:

(iii) reacting a diene copolymer of at least one $C_2$ to $C_{22}$ alpha olefin and at least one conjugated or non-conjugated diene with a hydroboration reagent to incorporate borane-containing units into the diene copolymer chain; and (iv) contacting the borane-containing diene copolymer formed in step (iii) with at least one free radically polymerizable monomer in the presence of an oxidative reagent to convert at least one of said borane-containing units to a free radical which, in turn, initiates free radical polymerization of said free radically polymerizable monomer, thereby forming said graft copolymer having the formula II.

2. The graft copolymer of claim 1, wherein (c) is 0 and (b) is at least one.

3. The graft copolymer of claim 2 wherein the x units are derived from one or a mixture of alpha monoolefins having from 2 to about 22 carbon atoms.

4. The graft copolymer of claim 3 wherein said monoolefins are selected from the group consisting of ethylene, propylene, 1-butene, 1-octene, isobutylene and mixtures thereof.

5. The graft copolymer of claim 4 wherein said monoolefin is propylene.

6. The graft copolymer of claim 4 wherein said monoolefin is isobutylene.

7. The graft copolymer of claim 4 wherein said monoolefin is 1-octene.

8. The graft copolymer of claim 4 wherein said monoolefin is a mixture of ethylene and propylene.

9. The graft copolymer of claim 2 wherein $R_3$ is a divalent hydrocarbon containing from 3 to about 12 carbon atoms.

10. The graft copolymer of claim 2 wherein (a) is 0.

11. The graft copolymer of claim 2 having formula II wherein the x units are derived from isobutylene and the diene units are derived from isoprene.

12. The graft copolymer of claim 2 having the formula II wherein the x units are derived from a mixture of ethylene and propylene and the diene units are derived from a non-conjugated diolefin.

13. The graft copolymer of claim 2 wherein said M units are based on a free radically polymerized monomer selected from the group consisting of alkyl acrylates and methacrylates, acrylic and methacrylic acid, vinyl aromatic compounds, vinyl amides, vinyl pyridines, acrylonitriles, vinyl acetates, vinyl chloride and vinylidene chloride and mixtures thereof.

14. The graft copolymer of claim 13 wherein said M units are selected from the group consisting of styrene, methyl methacrylate and t-butyl methacrylate.

15. The graft copolymer of claim 2 having a number average molecular weight in the range of from about 50,000 to about 3,000,000 and wherein said $(M)_n$ units comprise from about 5 to about 95% by weight of the copolymer composition.

16. The graft copolymer of claim 2 wherein (a) is greater than 0 and W is selected from the group consisting of $NH_2$, CHO, OH and halogen.

17. The graft copolymer of claim 2 wherein (a) is greater than 0 and W is $BR_4R_5$ wherein $R_4$ and $R_5$ are the same or different alkyl or cycloalkyl groups containing 1 to 10 carbon atoms.

* * * * *